US009209096B2

(12) United States Patent
Allenic et al.

(10) Patent No.: US 9,209,096 B2
(45) Date of Patent: Dec. 8, 2015

(54) PHOTOLUMINESCENCE MEASUREMENT (75) Inventors: Arnold Allenic, Ann Arbor, MI (US);
Douglas Bacon, Palo Alto, CA (US);
Benyamin Buller, Sylvania, OH (US);
John Christiansen, Perrysburg, OH (US);
Erel Milshtein, Cupertino, CA (US);
Avner Regev, Gan Yavne (IL);
Igor Sankin, Perrysburg, OH (US)

(73) Assignee: FIRST SOLAR, INC, Perrysburg, OH (US)

( * ) Notice: Subject to any disclaimer, the term of this patent is extended or adjusted under 35 U.S.C. 154(b) by 730 days.

(21) Appl. No.: 13/195,163

(22) Filed: Aug. 1, 2011

(65) Prior Publication Data

US 2012/0025100 A1  Feb. 2, 2012

Related U.S. Application Data (60) Provisional application No. 61/369,141, filed on Jul. 30, 2010.

(51) Int. Cl.
*G01J 1/58* (2006.01)
*H01L 21/66* (2006.01)
*G01N 21/64* (2006.01)
*G01N 21/95* (2006.01)
*G01N 21/84* (2006.01)

(52) U.S. Cl.
CPC ............ *H01L 22/12* (2013.01); *G01N 21/6489* (2013.01); *G01N 21/9501* (2013.01); *G01N 2021/646* (2013.01); *G01N 2021/6419* (2013.01); *G01N 2021/6421* (2013.01); *G01N 2021/845* (2013.01); *G01N 2021/8411* (2013.01)

(58) Field of Classification Search
CPC ... G01J 1/58; G01N 21/6428; G01N 21/6458; G01N 21/9501
USPC ............ 250/362, 361 R, 492.2, 458.1, 459.1; 356/237.1, 237.4
See application file for complete search history.

(56) References Cited

U.S. PATENT DOCUMENTS

| 3,326,730 | A | * | 6/1967 | Mandel et al. ................ 438/544 |
| 4,562,356 | A | | 12/1985 | Auth |
| 4,572,668 | A | | 2/1986 | Auth |
| 4,661,770 | A | | 4/1987 | von Roos |
| 4,744,663 | A | | 5/1988 | Hamashima et al. |
| 4,978,862 | A | * | 12/1990 | Silva et al. ............... 250/559.45 |
| 5,153,503 | A | | 10/1992 | Yahata |
| 5,302,832 | A | | 4/1994 | Kitagawara et al. |

(Continued)

FOREIGN PATENT DOCUMENTS

| AU | 2006301905 A1 | 4/2007 |
| CN | 1279398 A | 1/2001 |

(Continued)

OTHER PUBLICATIONS

P. Würfel et al., "Diffusion Lengths of Silicon Solar Cells from Luminescence Images," Journal of Applied Physics, vol. 101, pp. 123110-1-123110-10, 2007.

(Continued)

*Primary Examiner* — Marcus Taningco
*Assistant Examiner* — Djura Malevic
(74) *Attorney, Agent, or Firm* — Dickstein Shapiro LLP (57) ABSTRACT A photoluminescence measurement system can include an optical source.

34 Claims, 2 Drawing Sheets

(56) References Cited

U.S. PATENT DOCUMENTS

| | | | |
|---|---|---|---|
| 5,381,016 A | 1/1995 | Moriya | |
| 5,539,514 A * | 7/1996 | Shishido et al. | 356/237.4 |
| 5,841,532 A | 11/1998 | Yoshida et al. | |
| 5,995,217 A * | 11/1999 | Watanabe | 356/237.1 |
| 6,081,127 A | 6/2000 | Wagner et al. | |
| 6,084,664 A | 7/2000 | Matsumoto et al. | |
| 6,091,488 A | 7/2000 | Bishop | |
| 6,108,079 A * | 8/2000 | Maeshima et al. | 356/237.2 |
| 6,153,444 A | 11/2000 | Nakano et al. | |
| 6,160,615 A * | 12/2000 | Matsui et al. | 356/237.4 |
| 6,256,092 B1 * | 7/2001 | Tomita et al. | 356/237.1 |
| 6,359,686 B1 * | 3/2002 | Ariglio et al. | 356/239.1 |
| 6,534,774 B2 | 3/2003 | Hasegawa et al. | |
| 6,683,683 B2 | 1/2004 | Tomita et al. | |
| 7,038,768 B2 | 5/2006 | Takeuchi et al. | |
| 7,113,276 B1 | 9/2006 | Higgs | |
| 7,139,083 B2 * | 11/2006 | Fielden et al. | 356/630 |
| 7,245,696 B2 * | 7/2007 | Yun et al. | 378/45 |
| 7,446,321 B2 * | 11/2008 | Laurent et al. | 250/458.1 |
| 7,504,642 B2 * | 3/2009 | Hummel et al. | 250/458.1 |
| 7,567,343 B2 | 7/2009 | Ohshima et al. | |
| 7,852,473 B2 | 12/2010 | Wolff | |
| 8,330,946 B2 * | 12/2012 | Buczkowski et al. | 356/237.1 |
| 8,629,411 B2 * | 1/2014 | Beck et al. | 250/458.1 |
| 2002/0054295 A1 * | 5/2002 | Maris | 356/496 |
| 2005/0163637 A1 * | 7/2005 | Chang et al. | 417/476 |
| 2006/0237811 A1 | 10/2006 | Thomas et al. | |
| 2006/0241872 A1 | 10/2006 | Gilmore et al. | |
| 2007/0000434 A1 | 1/2007 | Buczkowski | |
| 2007/0007466 A1 * | 1/2007 | Laurent et al. | 250/458.1 |
| 2007/0008518 A1 * | 1/2007 | Hummel et al. | 356/237.1 |
| 2007/0008526 A1 | 1/2007 | Buckowski | |
| 2007/0176119 A1 * | 8/2007 | Hummel | 250/458.1 |
| 2007/0289627 A1 * | 12/2007 | Singh et al. | 136/264 |
| 2008/0023336 A1 * | 1/2008 | Basol | 205/182 |
| 2009/0051914 A1 | 2/2009 | Trupke et al. | |
| 2009/0206287 A1 | 8/2009 | Trupke et al. | |
| 2009/0224175 A1 | 9/2009 | Lee et al. | |
| 2010/0006785 A1 | 1/2010 | Finarov | |
| 2010/0025588 A1 | 2/2010 | Trupke et al. | |
| 2010/0089884 A1 * | 4/2010 | Sercel et al. | 219/121.72 |
| 2010/0129942 A1 | 5/2010 | Yamaguchi et al. | |
| 2011/0001142 A1 | 1/2011 | Saitoh | |
| 2011/0139240 A1 * | 6/2011 | Allenic et al. | 136/256 |

FOREIGN PATENT DOCUMENTS

| | | |
|---|---|---|
| DE | 102007057011 | 6/2009 |
| EP | 2284520 | 2/2011 |
| JP | 63156332 | 6/1988 |
| JP | 63312649 | 12/1988 |
| JP | 1094247 | 4/1989 |
| JP | 2000252338 | 9/2000 |
| JP | 2001013073 | 1/2001 |
| WO | WO 2008/014537 A1 | 2/2008 |
| WO | WO 2008/014537 A1 | 2/2008 |
| WO | WO/2010/110751 | 9/2010 |
| WO | WO/2011/017775 | 2/2011 |
| WO | WO/2011/017776 | 2/2011 |

OTHER PUBLICATIONS

T. Trupke et al., "Photoluminescence Imaging of Silicon Wafers," Applied Physics Letters, vol. 89, pp. 044107-1-044107-3, 2006.
Second Office Action issued on Apr. 29, 2015 in CN Application No. 201180043029.2.

* cited by examiner

PHOTOLUMINESCENCE MEASUREMENT

This application claims priority under 35 U.S.C. §119(e) to Provisional Application No. 61/369,141, filed on Jul. 30, 2010, which is incorporated herein by reference.

TECHNICAL FIELD

This invention relates to a photoluminescence measurement tool and system.

BACKGROUND

Photoluminescence (PL) is a process in which a substance absorbs photons (electromagnetic radiation) and then re-radiates photons. Photoluminescence measurement is a contactless, nondestructive method of probing the electronic structure of materials. Improved PL measurement tools and systems integrated into a photovoltaic module manufacturing process would be desirable.

DETAILED DESCRIPTION

Photovoltaic cells can include multiple layers created on front support such as a substrate or superstrate. For example, a photovoltaic cell can include a barrier layer, a transparent conductive oxide (TCO) layer, a buffer layer, and a semiconductor layer formed in a stack on a substrate. Each layer may in turn include more than one layer or film. For example, the semiconductor layer can include a first film including a semiconductor window layer formed on the buffer layer and a second film including a semiconductor absorber layer formed on the semiconductor window layer. Additionally, each layer can cover all or a portion of the device and/or all or a portion of the layer or substrate underlying the layer. For example, a "layer" can include any amount of any material that contacts all or a portion of a surface.

Photoluminescence measurement is a contactless, nondestructive method of probing the electronic structure of materials, such as materials included in the layers of photovoltaic cells. Light is directed onto a sample, where it is absorbed and imparts energy into the material in a process called photo-excitation. This energy can be dissipated by the sample is through the emission of light, or luminescence. The intensity and spectral content of this photoluminescence is a direct measure of various fundamental material properties. A photoluminescence measurement system and related method are developed for the semiconductor device manufacturing (e.g. photovoltaic device).

Photo-excitation causes electrons within the material to move into permissible excited states. When these electrons return to their equilibrium states, the excess energy is released and may include the emission of light (a radiative process). The energy of the emitted light (photoluminescence) relates to the difference in energy levels between the two electron states involved in the transition between the excited state and the equilibrium state. The quantity of the emitted light is related to the relative contribution of the radiative process.

Photoluminescence measurement can be used to determine a semiconductor's band gap. The most common radiative transition in semiconductors is between states in the conduction and valence bands, with the energy difference being known as the band gap. Band gap determination is particularly useful when working with new compound semiconductors.

Photoluminescence measurement can be used to detect semiconductor impurity levels and defect levels. Radiative transitions in semiconductors can also involve localized defect levels. The photoluminescence energy associated with these levels can be used to identify specific defects, and the amount of photoluminescence can be used to determine their concentration.

Photoluminescence measurement can be used to study semiconductor recombination mechanisms. The return to equilibrium, also known as "recombination," can involve both radiative and nonradiative processes. The amount of photoluminescence and its dependence on the level of photo-excitation and temperature are directly related to the radiative recombination process. Analysis of photoluminescence helps to understand the underlying physics of the recombination mechanism.

Photoluminescence measurement can be used to measure semiconductor material quality. In general, nonradiative processes are associated with localized defect levels, whose presence is detrimental to material quality and subsequent device performance. Thus, material quality can be measured by quantifying the amount of radiative recombination.

Therefore, a photoluminescence measurement system and related method are developed for the semiconductor device manufacturing (e.g. photovoltaic device), specifically when more than one semiconductor layer is formed. For example, in photovoltaic device manufacturing, non-destructive measurements of the semiconductor layers are required to optimize solar module performance, spatial uniformity, and temporal stability. The in-line photoluminescence measurement system can measure photoluminescence at multiple wavelengths and spatial locations in real time.

This non-destructive technique can use light to excite electrical carriers in the semiconductor. When these excited carriers decay, light is emitted. The incident light must have energy greater than the energy transition that is to be monitored. The resultant luminescent light energy and intensity can provide information on the electrical states in the p-type and n-type semiconductor layers. Varying the incident wavelength can facilitate investigation of different semiconductor layers. Performing this measurement at multiple spatial locations and with multiple wavelengths of incident light allows for in situ measurements of electrical performance, uniformity, and predictions of device performance stability.

In some embodiments, this measurement system can be used at multiple points in a semiconductor device (e.g. solar module) production line. This can be done from the semiconductor film side of the device in either a substrate or superstrate configuration, or through a transparent substrate in a superstrate configuration.

In one aspect, a photoluminescence measurement tool can include a first optical source for generating a first optical radiation to illuminate a first semiconductor material of a substrate. The first semiconductor material can be excited by the first optical radiation and emits a first luminescent radiation. The tool can include a first sensor. The first luminescent radiation can radiate from the first semiconductor material of the substrate to the first sensor.

The tool can include a first lens optically connected to the first sensor. The first luminescent radiation can radiate from the semiconductor material of the substrate through the first lens to the first sensor. The tool can include a second optical source for generating a second optical radiation to illuminate a second semiconductor material of the substrate. The second semiconductor material can be excited by the second optical radiation and emits a second luminescent radiation. The tool can include a second sensor. The second luminescent radiation can radiate from the second semiconductor material of the substrate to the second sensor.

The tool can include a second lens optically connected to the second sensor. The second luminescent radiation can radiate from the second semiconductor material of the substrate through the second lens to the second sensor. The tool can include an analyzing module for analyzing the energy and intensity of the first and second luminescent radiations to obtain the information on the electrical states of the first and second semiconductor materials. The first and second optical sources can be capable to generate an optical radiation of a plurality of wavelengths and the wavelengths of the first and second optical radiations are chosen based on the band gaps of the semiconductor materials.

The first and second sensors can be capable to measure an optical radiation of a plurality of wavelengths generated by the optical sources. The tool can be an in situ configuration for illuminating different sample locations of the semiconductor material to obtain spatial measurements of electrical performance, uniformity, and predictions of device performance stability. The tool can include at least one filter. The filter can reduce the variance of the wavelength distribution of the optical radiation from the optical source.

The tool can include a first optical system. The first optical system can transform the first and second optical radiations from the first and second optical sources to collimated or focused beams of photons and reduces the variance of the wavelength distribution of the first and second optical radiations from the first and second optical sources. The first optical system can include at least one plano-convex lens and a band pass filter. The band pass filter can be positioned between the first optical source and the first optical system. The tool can include a second optical system. The second optical system can transform the first and second luminescent radiations from the semiconductor materials of the substrate to focused beams of photons focusing on the first and second sensors. The second optical system can include a filter selected from a group consisting of long pass filter, short pass filter, band pass filter and any combination of these filters. The combination of these filters can allow only a specific region of the wavelength distribution of the luminescent radiations from the semiconductor materials of the substrate to be detected by the first and second sensors.

At least one of the first optical system and the second optical system can include a dichroic mirror. The dichroic mirror can be oriented at an angle to reflect light from the first or second optical source or light source along a path substantially perpendicular to a substrate position where a substrate including a semiconductor coating can be positioned. The dichroic mirror can be transmissive to photoluminescent radiation reemitted from a semiconductor material on a substrate at the substrate position. The dichroic mirror can allow the photoluminescent radiation to be detected by the first or second sensors. The semiconductor materials of the substrate can include a bilayer of semiconductor material. The optical sources can include a laser diode. The optical sources can include a light-emitting diode. The substrate can be transported on a conveyor. The tool can include an encoder for tracking of conveyor movement and positioning on the substrate. The sensors can include a photodiode. The sensors can include a photomultiplier tube.

In another aspect, an in-line method of real-time measuring photoluminescence of semiconductor material can include transporting a substrate to a measure position by a conveyor and generating a first optical radiation of a first wavelength to illuminate a first sample area of a multi-layer semiconductor material of the substrate by an optical source. A first semiconductor layer can be excited by the first optical radiation and emits a first luminescent radiation. The method can include measuring the first luminescent radiation by a sensor and analyzing the energy and intensity of the first luminescent radiation to obtain the information on the electrical state of the first semiconductor layer.

The method can include generating a second optical radiation of a second wavelength to illuminate the first sample area of the multi-layer semiconductor material of the substrate by the optical source. A second semiconductor layer can be excited by the second optical radiation and emits a second luminescent radiation. The method can include measuring the second luminescent radiation by the sensor and analyzing the energy and intensity of the second luminescent radiation to obtain the information on the electrical state of the second semiconductor layer.

The wavelengths of the first and second optical radiations can be chosen based on the band gaps of the semiconductor layers. The method can include reducing variance of the wavelength distribution of the optical radiation from the optical source. The method can include transforming the optical radiation from the optical source to a focused or collimated beam of photons by a first optical system. The first optical system can include at least one plano-convex lens and a band pass filter.

The method can include transforming the luminescent radiation from the semiconductor material of the substrate to a focused beam of photons focusing on the sensor by a second optical system. The second optical system can include a filter selected from a group consisting of long pass filter, short pass filter, band pass filter and any combination of these filters, the combination of these filters allowing only a specific region of the wavelength distribution of the luminescent radiation from the semiconductor material of the substrate to be detected by the sensor. The method can include directing the optical radiation from the optical source to the semiconductor material of the substrate and directing the luminescent radiation from the semiconductor material of the substrate to the sensor by at least one optical mirror.

In another aspect, a photoluminescence measurement system for monitoring and controlling a photovoltaic module manufacturing process can include at least one optical source for generating at least one optical radiation to illuminate at least one semiconductor material of a substrate. The semiconductor material can be excited by the optical radiation and emits at least one luminescent radiation. The system can include at least one sensor, wherein the luminescent radiation radiates from the semiconductor material of the substrate to the sensor and an analyzing module for analyzing the energy and intensity of the luminescent radiation to obtain the information on the electrical states of the semiconductor material.

The substrate can be transported on a conveyor. The system can be configured to measure the semiconductor material when the substrate is in motion. The system can include a feed-back control loop. The system can adjust the photovoltaic module manufacturing process when the process is deviating and causing the production of non conforming module. The system can include a decoding module for tracking conveyor movement and assigning each measured photoluminescent signal to a specific location on the substrate.

Figure 1:
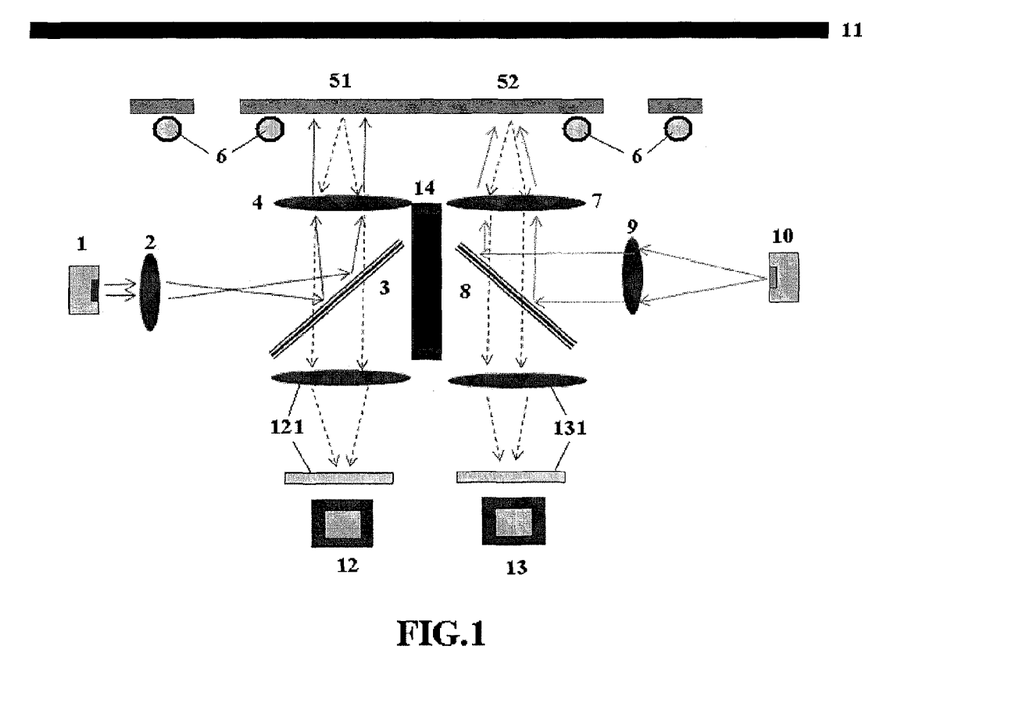
FIG. 1 is a diagram illustrating a photoluminescence measurement system.

Referring to FIG. 1, a measurement system can include monochromatic light sources 1 and 10. Light source 1 or 10 can be any suitable light source, such as a light emitting diode, a diode laser or a solid state laser. Light source 1 or 10 can also consist of a white light source placed ahead of a monochromator. The wavelength of light source 1 or 10 can be chosen based on the band gap of one or more semiconductor materials deposited at first location 51 and second location 52 to be measured. The measurement system can include optical systems 2 and 9 having lenses and filters. Optical systems 2 and 9 can supply a focused and/or collimated beam of photons. It can also reduce the variance of the wavelength distribution. It can for example consist of at least one plano-convex lens and a band pass filter. The band pass filter can be positioned between light sources 1 or 10 and their respective optical systems 2 or 9, or can be integrated into optical systems 2 or 9 or any other suitable position. The band pass filter or filters can be optional, and the decision to include a band pass filter can be based on the coherence of the light from the light source.

The measurement system can include optical mirrors 3 and 8 used to redirect the photonic beams toward semiconductor material or materials at first and second substrate locations 51 and 52. The measurement system can include lens 4 and 7. Lens 4 and 7 can be chosen and positioned so that first and second substrate locations 51 and 52 are in the image plan of lens 4 and 7. In some embodiments, slight under- or overfocus can be acceptable. Lens 4 and 7 can be optional depending on beam collimation, distance to the semiconductor material or desired fluence levels.

Light source 1 can include any suitable light source, including a diode, solid state laser, or LED. Light source 1 can emit light of any suitable wavelength. For example, light source 1 can emit red light. Light source 1 can emit light having a wavelength between about 630 nm and about 690 nm. Light source 1 can emit light having a wavelength of about 660 nm. Light source 10 can include any suitable light source, including a diode laser, solid state laser, or LED. Light source 10 can emit light of any suitable wavelength. For example, light source 10 can emit blue light. Light source 10 can emit light having a wavelength between about 440 nm and about 490 nm. Light source 10 can emit light having a wavelength of about 470 nm.

Semiconductor materials at first and second substrate locations 51 and 52 can be deposited on the substrate, which can include any suitable substrate such as transparent conducting oxide coated glass substrates. Semiconductor materials at one or both of first and second substrate locations 51 and 52 can be excited by the beam of photons at its surface or from its interface with the substrate. The process of light emission following excitation of the semiconductor with light of energy greater than its band gap can be called photoluminescence. It is a result of recombination of photogenerated carriers. Light emission depends on internal and external quantum efficiencies of each semiconductor layer. If the excited device consists of a bilayer of material, for example a p-type semiconductor deposited on an n-type semiconductor, recombination can occur at various locations depending on the excitation light intensity, wavelength and resulting depth of penetration into the bilayer. The measurement system can include transport conveyors 6, such a conveyor transporting solar modules on a production line. This in-line configuration can allow in-cycle measurements of semiconductor photoluminescence. In some embodiments, an off-line replica of this system for rapid batch evaluation can also be utilized in a research and development environment.

Semiconductor materials at first substrate location 51 can include material in a semiconductor absorber layer. Semiconductor material at first substrate location 51 can include cadmium telluride or any other suitable semiconductor absorber material. Semiconductor material at second substrate location 52 can include material in a semiconductor window layer. Semiconductor material at second location 52 can include cadmium sulfide or any other suitable semiconductor window material. The photoluminescence measurement system can measure luminescence properties of two distinct materials and thus can measure a semiconductor absorber layer (for example a cadmium telluride layer) and a semiconductor window layer (for example a cadmium sulfide layer) simultaneously.

The two distinct materials can be measured using light from the two light sources 1 and 10. For example, light from light source 1 can be used for cadmium telluride while light from light source 10 can be used for cadmium sulfide. For example, as the substrate moves relative to the photoluminescence measurement tool (e.g., left to right in FIG. 1), cadmium telluride at second substrate location 52 will pass adjacent to light source 1 and its associated mirror. Thus, cadmium telluride at second substrate location 52 is photoluminescence-analyzed. Then, as the substrate passes the system, second substrate location 52 moves adjacent to light source 10 and its associated mirror. At that point, a second semiconductor material, for example cadmium sulfide which can be formed in a layer adjacent to the cadmium telluride layer on the substrate, can be analyzed by light source 10 and its associated mirror and detector. Simultaneously, cadmium telluride at substrate location 51 can be observed by light source 1 since it is adjacent to light source 1 and in the path of light from light source 1. In this way, multiple materials at multiple locations (or a single material at multiple locations) can be analyzed continuously as the substrate is conveyed past the photoluminescence measurement system.

Semiconductor materials at first and second substrate locations 51 and 52 can also include a mixture of more than one semiconductor. For example, semiconductor materials at first and second substrate locations 51 and 52 can include a mixture of cadmium telluride and cadmium sulfide (represented, for example, by the formula $CdTe_xS_{1-x}$). Such mixtures can occur at the interface of a cadmium telluride layer and a cadmium sulfide layer in a photovoltaic device. Intermixed materials such as this can be analyzed by the photoluminescence measurement system as the substrate moves through the manufacturing process.

The measurement system can include sensors 12 and 13. Optical systems 121 and 131 having any suitable combination of lenses and/or filters can be positioned in front of sensors 12 and 13. The combination of these filters can allow only a specific region of the wavelength distribution of the luminescent radiations from the semiconductor materials of the substrate to be detected by the first and second sensors. Optical systems 121 and 131 can supply focused and/or collimated beams of luminescent radiation to be measured by sensors 12 and 13. It can also reduce the variance of the wavelength distribution. The measurement system can include optical mirror 8 used to redirect the luminescent radiation. The measurement system can include lens 7. Lens 7 can be chosen and positioned so that the luminescent radiation from semiconductor material at second substrate location 52 is in the image plane of lens 7. Sensors 12 and 13 can include a photodetector being used in photocurrent mode but can also be used in photon counting mode. A diffraction gratings with two mirrors can be added for spectral separation of the photocurrent source. The measurement system can include opaque and non reflective lid 11 used to protect tool user from optical radiation.

Light from light sources 1 and 10 can be transformed as necessary (e.g., collimated or focused) toward semiconductor materials at first and second substrate locations 51 and 52 through any suitable lenses or lens systems, e.g., lenses 4 and 7. For example, light from light source 1 can be collimated by lens 4 toward a cadmium telluride semiconductor material at first substrate location 51. The collimated beam can have a spot diameter of less than about 20 mm on cadmium telluride semiconductor material at first substrate location 51, for example a spot diameter of about 10 mm. Light from light source 10 can be focused by lens 7 toward cadmium sulfide semiconductor material at second substrate location 52. The focused beam can have a spot diameter of less than about 30 mm on cadmium sulfide semiconductor material at second substrate location 52. The focused beam can have a spot diameter of about 4 mm to about 20 mm on cadmium sulfide semiconductor material at second substrate location 52.

Shield or beam dump 14 can be included in the middle of the measurement system to prevent any interference of light sources and sensors.

In some embodiments, the forward emitted luminescence can be collected by lenses 4 and 7 and collimated in the direction of optical systems 121 and 131. Mirrors 3 and 8 can be dichroic. Mirrors 3 and 8 can reflect the LED/laser wavelengths but are transparent to the range of wavelengths emitted by the semiconductor layers. Optical systems 121 and 131 can include a convex lens and a sensor/photodetector lying in the image plane of that lens.

Mirrors 3 and 8 and optionally other components of the luminescence measurement system can be incorporated into an optical head to be deployed in a photovoltaic module manufacturing process. The compact nature of the optical head can be attributed in part to the use and orientation of dichroic mirrors, which enable the optical radiation to be transmitted through the same structure from which it is emitted. In some embodiments, the optical heads can be positioned on a compact backing (for example, a backing measuring between about 6" and 12" by between about 6" and 12", such as a backing measuring about 8" by about 10"). Because they are be configured so compactly, the optical heads can be flexibly integrated into a photovoltaic module manufacturing process. For example, the optical head can be positioned in any suitable configuring or position relative to a substrate onto which semiconductor materials at first and second substrate locations 51 and 52, for example, have been deposited and are ready to be analyzed.

It should be noted that mirrors 3 and 8 can be oriented at an angle that allows them to reflect light from their respective light sources 1 and 10 along a path perpendicular to the surface of a substrate including semiconductor materials at first and second substrate locations 51 and 52 for analysis. Because mirrors 3 and 8 can be dichroic, they can be transmissive to photoluminescent radiations reemitted from semiconductor materials at first and second substrate locations 51 and 52, back through the optical head and toward sensors positioned proximate to optical systems 121 and 131, through which the photoluminescent radiation can travel (and focused, if necessary) in order to be measured.

In some embodiments, light sources 1 and 10 can, emit light beams of different wavelengths to measure at least two different semiconductor materials (at first and second substrate locations 51 and 52). In some embodiments, light sources 1 and 10 can emit light beams of same wavelength to measure one semiconductor material at two different locations on the substrate. The measurement system can further use the readings of sensors 12 and 13 to monitor and adjust the semiconductor material deposition process or moving speed of conveyor 6.

Figure 2:
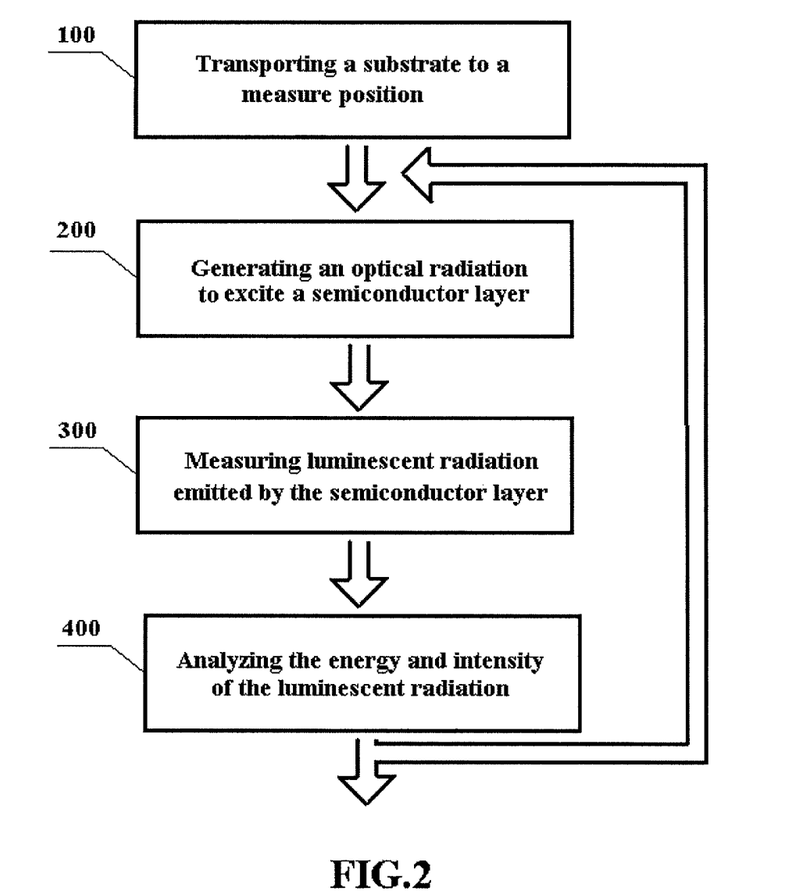
FIG. 2 is a flow chart illustrating a working process of a photoluminescence measurement system.

Referring to FIG. 2, a measuring process of a measurement system with an in-line configuration can include the following steps: step 100 of transporting a substrate to a measure position by a conveyor; step 200 of generating an optical radiation to illuminate a sample area of a semiconductor layer which can be excited by the optical radiation and emits a luminescent radiation; step 300 of measuring the luminescent radiation by a sensor; and step 400 of analyzing the energy and intensity of the luminescent radiation to obtain the information on the electrical state of the semiconductor layer. The wavelength of the optical radiation is chosen based on the band gap of the semiconductor layer.

As shown in FIG. 2, when a multi-layer semiconductor material is measured, the measuring steps 100-400 can be repeated with another optical radiation having a different wavelength to excite a different semiconductor layer. Based on the structure of multi-layer semiconductor material, the measuring steps 100-400 can be repeated multiple times till all the semiconductor layers have been measured. The wavelengths of the optical radiations can be chosen based on the different band gaps of the multiple semiconductor layers.

In some embodiments, the wavelength of light source can be in the red or blue range of the visible spectrum of light. Choice of wavelength depends on the band gap of the semiconductor material to be measured. In solar module manufacturing, the measurement system can be used as a predictor of module long-term performance.

In solar module manufacturing, the measurement system can be used to monitor process-driven non uniformities within solar module. For example, CdTe and CdS layers can be deposited on a TCO-coated glass. The bilayer stack needs to go through an activation anneal which serves numerous purposes, some of which are absorber grain recrystallization, passivation of surface/interface states, electronic doping and CdTe/CdS intermixing. Due to its complexity and due to the size of the coated substrates fed into the oven, this process can activate the semiconductor layers in a non uniform manner. In some embodiments, the measurement system can be configured to measure multiple line scans along both directions of the substrate. For example, the activation anneal can yield significant variations of the semiconductor optoelectronic properties within the same module. These can be easily and immediately detected by the photoluminescence measurement system. The data can be fed into a closed loop control and used to modulate the oven parameters if the oven deviates from its purported baseline.

The measurement system can be used as a process control tool. It can be used to trigger an out of control action plan, when either the semiconductor layer deposition tool or the semiconductor layer activation tool deviate from their purported baseline and pose a risk to module electrical performance or stability. In some embodiments, if control limits exist on certain electronic properties of the absorber or the window layer, and if a process is deviating from its purported baseline, the measurement system can be used as indicator that the process is deviating and causing the production of non conforming product. The process parameters can be adjusted to bring the tools back in control based on the signals measured by the in line photoluminescence measurement system.

The measurement system can be used as a module IV parameters predictor. In some embodiments, it can take three hours to build a solar module on the production line, and if the measurement system can be set up early on the line, final IV parameters of modules can be predicted early. If the effects of various processes on IV parameters need to be isolated, more than one metrology tool can be installed to facilitate partition of variance. Correlations to the main junction open circuit voltage can be observed too. Fundamental device performance metrics such as interface recombination and absorber bulk recombination can be evaluated. The measurement system can be used to monitor electronic properties and estimate final IV parameters before the modules are boxed up and shipped off-site.

As quality inspection tool, the metrology tool can raise the flag on a process, when it is out of control or about to deviate from its purported baseline and cause serious risks in terms of module performance and stability. It can be used to monitor distributions of structural, electronic and optical properties within a module and ensure that a process is not causing within-module excursions. The measurement system can prevent production of out of control or scrap material by immediate trigger of OCAPs. The measurement system can prevent distribution of non conforming modules. The measurement system can flag process excursions otherwise invisible. It can differentiate potentially unstable modules from standard process of record modules, without the need for accelerated life tests, which are normally destructive and time consuming. With the measurement system installed on the line, immediate feedback and action can be taken to prevent NCP/quality risks. The measurement system can be used as global alignment tool, to minimize line-to-line variation.

A number of embodiments of the invention have been described. Nevertheless, it will be understood that various modifications may be made without departing from the spirit and scope of the invention. It should also be understood that the appended drawings are not necessarily to scale, presenting a somewhat simplified representation of various preferred features illustrative of the basic principles of the invention.

What is claimed is:

1. A photoluminescence measurement tool for measuring properties of at least two semiconductor materials, one overlying the other, on a photovoltaic module substrate, the tool comprising:
a first optical source for generating a first optical radiation to illuminate a first semiconductor material on a photovoltaic module substrate, the first optical radiation having a wavelength which is based on the bandgap of the first semiconductor material, wherein the first semiconductor material is excited by the first optical radiation and emits a first luminescent radiation;
a first sensor, wherein the first luminescent radiation radiates from the first semiconductor material of the photovoltaic module substrate to the first sensor;
a second optical source for generating a second optical radiation to illuminate a second semiconductor material on the photovoltaic module substrate, the second semiconductor material being different from and provided over the first semiconductor material, the second optical radiation having a wavelength which is based on the bandgap of the second semiconductor material, wherein the second semiconductor material is excited by the second optical radiation and emits a second luminescent radiation;
a second sensor, wherein the second luminescent radiation radiates from the second semiconductor material of the photovoltaic module substrate to the second sensor; and
a shield or beam dump positioned between the first optical source and second optical source;
wherein the first and second semiconductor materials are arranged one over the other on the photovoltaic module substrate and the luminescent radiations respectively characterize properties of the first and second semiconductor materials, and
wherein the first semiconductor material comprises an absorber layer and the second semiconductor material comprises a window layer.

2. The tool of claim 1 further comprising a first lens optically connected to the first sensor, wherein the first luminescent radiation radiates from the first semiconductor material of the photovoltaic module substrate through the first lens to the first sensor.

3. The tool of claim 2 further comprising a second lens optically connected to the second sensor, wherein the second luminescent radiation radiates from the second semiconductor material of the photovoltaic module substrate through the second lens to the second sensor.

4. The tool of claim 1, further comprising an analyzing module for analyzing the energy and intensity of the first and second luminescent radiations to obtain information on the electrical states of the first and second semiconductor materials.

5. The tool of claim 1, wherein the first and second optical sources are capable of generating an optical radiation of a plurality of wavelengths.

6. The tool of claim 5, wherein the first and second sensors are capable of measuring luminescence radiation produced by the plurality of wavelengths generated by the optical sources.

7. The tool of claim 1, wherein the tool can illuminate different sample locations of the first and second semiconductor materials to obtain spatial measurements of electrical performance, uniformity, and predictions of device performance stability.

8. The tool of claim 1, further comprising at least one filter in an optical path from at least one of the first and second optical sources, wherein the filter reduces the variance of the wavelength distribution of the optical radiation from the at least one optical source.

9. The tool of claim 1, further comprising a first optical system and a second optical system, wherein the first optical system and the second optical system transform the first and second optical radiations from the first and second optical sources to collimated or focused beams of photons and reduce the variance of the wavelength distribution of the first and second optical radiations from the first and second optical sources.

10. The tool of claim 9, wherein the first optical system comprises at least a first plano-convex lens and a first band pass filter, and the second optical system comprises at least a second plano-convex lens and a second band pass filter.

11. The tool of claim 10, wherein the first band pass filter is positioned between the first optical source and the first optical system, and the second band pass filter is positioned between the second optical source and second optical system.

12. The tool of claim 9, further comprising a third optical system and a fourth optical system, wherein the third optical system and the fourth optical system transform the first and second luminescent radiations from the first and second semiconductor materials of the photovoltaic module substrate to focused beams of photons focused on the first and second sensors.

13. The tool of claim 12, wherein the third optical system and the fourth optical system each comprise a filter selected from a group consisting of long pass filter, short pass filter, band pass filter and any combination of these filters, the filter allowing only a specific region of the wavelength distribution of the luminescent radiations from the first and second semiconductor materials on the photovoltaic module substrate to be detected by the first and second sensors.

14. The tool of claim 12, wherein at least one of the first optical system, the second optical system, the third optical system, and the fourth optical system comprises a dichroic mirror, wherein the dichroic mirror is oriented at an angle to reflect light from the first or second optical source along a path substantially perpendicular to a position where the photovoltaic module substrate can be positioned.

15. The tool of claim 14, wherein the dichroic mirror is transmissive to photoluminescent radiation reemitted from a semiconductor material on a substrate at the substrate position to allow the photoluminescent radiation to be detected by the first or second sensors.

16. The tool of claim 1, wherein at least one optical source comprises a laser diode.

17. The tool of claim 1, wherein at least one optical source comprises a light-emitting diode.

18. The tool of claim 1 further comprising a conveyor for transporting the photovoltaic module substrate past the first and second optical sources and first and second sensors.

19. The tool of claim 18, further comprising an encoder for tracking of conveyor movement and positioning of the photovoltaic module substrate.

20. The tool of claim 1, wherein at least one of the sensors comprises a photodiode.

21. The tool of claim 1, wherein at least one of the sensors comprises a photomultiplier tube.

22. The tool of claim 1, wherein the absorber layer comprises cadmium telluride and the window layer comprises cadmium sulfide.

23. An in-line method of real-time measuring photoluminescence of semiconductor material on a photovoltaic module substrate, the method comprising:
transporting the photovoltaic module substrate having at least a first semiconductor material and a second semiconductor material over the first semiconductor material to a measure position by a conveyor, and wherein the first semiconductor comprises an absorber layer and the semiconductor layer comprises a window layer;
generating a first optical radiation of a first wavelength to illuminate a sample area of the first semiconductor material by a first optical source, the first optical radiation having a wavelength which is based on the bandgap of the first semiconductor material, wherein the first semiconductor material is excited by the first optical radiation and emits a first luminescent radiation;
measuring the first luminescent radiation by a first sensor;
analyzing the energy and intensity of the first luminescent radiation to obtain the information on the electrical state of the first semiconductor material;
generating a second optical radiation of a second wavelength to illuminate a sample area of the second semiconductor material by a second optical source, the second semiconductor material being different from the first semiconductor material, the second optical radiation having a wavelength which is based on the bandgap of the second semiconductor material, wherein the second semiconductor layer is excited by the second optical radiation and emits a second luminescent radiation and wherein a shield or beam dump is positioned between the first optical source and the second optical source;
measuring the second luminescent radiation by a second sensor; and
analyzing the energy and intensity of the second luminescent radiation to obtain the information on the electrical state of the second semiconductor material.

24. The method of claim 23, further comprising reducing variance of the wavelength distribution of the optical radiations from the first and second optical sources.

25. The method of claim 23, further comprising transforming the optical radiation from the first and second optical sources to a focused or collimated beam of photons by first and second optical systems.

26. The method of claim 25, wherein at least one of the first and second optical systems comprise at least one plano-convex lens and a band pass filter.

27. The method of claim 25, wherein at least one of the first and the second optical system comprises a filter selected from a group consisting of long pass filter, short pass filter, band pass filter and any combination of these filters, the filter allowing only a specific region of the wavelength distribution of the luminescent radiation from the semiconductor material of the photovoltaic module substrate to be detected by an associated sensor.

28. The method of claim 23, further comprising directing the optical radiation from the first and second optical sources to the respective first and second semiconductor materials and directing the luminescent radiation from the first and second semiconductor materials to the respective first and second sensors through a third optical system and a fourth optical system.

29. The method of claim 23, wherein the photovoltaic module substrate is continuously in motion and allows for multiple line scans in both directions of the photovoltaic module substrate.

30. A photoluminescence measurement system for monitoring and controlling a photovoltaic module manufacturing process comprising:
a first optical source for generating a first optical radiation to illuminate a first semiconductor material on a photovoltaic module substrate, the first optical radiation having a wavelength which is based on the bandgap of the first semiconductor material, wherein the semiconductor material is excited by the optical radiation and emits at least one luminescent radiation;
a first sensor, for detecting first luminescent radiation radiating from the first semiconductor material; and
a second optical source for generating second optical radiation to illuminate a second semiconductor material on the photovoltaic module substrate, the second optical radiation having a wavelength which is based on the bandgap of the second semiconductor material, wherein the second semiconductor material is arranged over the first semiconductor material and is excited by the optical radiation and emits at least one luminescent radiation;
a second sensor, for detecting first luminescent radiation radiating from the second semiconductor material;
a shield or beam dump positioned between the first optical source and second optical source; and
an analyzing module for analyzing the energy and intensity of the luminescent radiation from the first and second semiconductor materials to obtain information on the electrical states of the semiconductor materials, and
wherein the first semiconductor material comprises an absorber layer and the second semiconductor material comprises a window layer.

31. The photoluminescence measurement system of claim 30, wherein the photovoltaic module substrate is transported on a conveyor.

32. The photoluminescence measurement system of claim 30, wherein the system is configured to measure the first and second semiconductor materials when the photovoltaic module substrate is in motion.

33. The photoluminescence measurement system of claim 30 further comprising a feed-back control loop, wherein the system adjusts a photovoltaic module manufacturing process when the process deviates from predetermined parameters as determined by the analyzing module.

34. The photoluminescence measurement system of claim 30 further comprising a decoding module for tracking conveyor movement and assigning each measured photoluminescent signal to a specific location on the photovoltaic module substrate.

* * * * *